(12) United States Patent
Olivarez (10) Patent No.: US 10,159,779 B2
(45) Date of Patent: Dec. 25, 2018

(54) VITAL SLEEVE

(71) Applicant: Antionette Olivarez, San Fernando, CA (US)

(72) Inventor: Antionette Olivarez, San Fernando, CA (US)

(*) Notice: Subject to any disclaimer, the term of this patent is extended or adjusted under 35 U.S.C. 154(b) by 0 days.

(21) Appl. No.: 15/972,225

(22) Filed: May 6, 2018

(65) Prior Publication Data

US 2018/0250463 A1    Sep. 6, 2018

Related U.S. Application Data

(63) Continuation-in-part of application No. 14/996,519, filed on Jan. 15, 2016.

(60) Provisional application No. 62/156,621, filed on May 4, 2015.

(51) Int. Cl.
  *A61B 5/04* (2006.01)
  *A61B 5/02* (2006.01)
  *A61M 1/36* (2006.01)
  *A61B 5/00* (2006.01)

(52) U.S. Cl.
  CPC ........ *A61M 1/3655* (2013.01); *A61M 1/3661* (2014.02); *A61B 5/6824* (2013.01)

(58) Field of Classification Search
  USPC .................................. 600/309, 508
  See application file for complete search history.

(56) References Cited

U.S. PATENT DOCUMENTS

| | | | |
|---|---|---|---|
| 2009/0082647 A1* | 3/2009 | Busby | A61M 1/3653 600/309 |
| 2010/0191166 A1* | 7/2010 | Phillips | A61B 17/0057 604/6.16 |
| 2011/0172692 A1* | 7/2011 | Wu | A61M 1/3655 606/191 |
| 2016/0296690 A1* | 10/2016 | Kume | A61M 39/06 |

* cited by examiner

*Primary Examiner* — Nicole F Johnson
(74) *Attorney, Agent, or Firm* — RG Patent Consulting, LLC; Rachel Gilboy (57) ABSTRACT

A combination of an AV shunt for hemodialysis patients and a protective sleeve that protects the shunt and the shunt site. The sleeve includes a clear window and technology to monitor and detect a weakening pulse, allowing for early intervention before more serious problems develop.

15 Claims, 6 Drawing Sheets

VITAL SLEEVE

CROSS-REFERENCE TO RELATED APPLICATION

The present application is related to and claims priority from prior provisional application Ser. No. 62/156,621, filed May 4, 2015 and prior Non-Provisional application Ser. No. 14/996,519, filed Jan. 15, 2016 which is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

1. Field of the Invention

The present invention generally relates to medical arm sleeve and in particular an arm sleeve for monitoring vital signs and protecting the shunt or fistula site in the arm of a patient.

2. Background of the Invention

Patients who have an injury to a particular area, or site, on the body which requires a relatively long healing time and/or protection from external elements, or who have a medical condition which requires access to a port site for periodic administration of medication, often have difficulty protecting these sites from contamination or damage due to external influences. These sites are usually fragile and painful to touch or pressure. One such site may be a wound, perhaps requiring stitches or administration of topical medication under a sterile dressing to facilitate the healing process. However, exposure to external elements is often detrimental to the healing process, even when the site is covered by a sterile dressing. Likewise, before starting hemodialysis treatments, one important step is preparing a vascular access, which is the site on your body where blood will be removed and returned during dialysis. For most people, an arteriovenous (AV) fistula is the best kind of vascular access. An AV fistula is created surgically by connecting an artery directly to a vein, usually in the forearm of patients. Then the vein grows larger and stronger, making repeated needle insertions easier. However, the regular hemodialysis sessions occur 2-3 times per week. In the long run, there could be hundreds of pinholes concentrate on the fistula which is only several centimeters in length. Thus, the repeated use of the fistula is likely to cause clots or infection and that may result in frequent replacement of fistula, via surgical intervention. The general way for improving the life of fistula/shunt and protecting the arm with fistula thereof is to use the arm for hemodialysis and not for other medical procedures. Further, avoiding any external pressure or assaults on arm may help to keep the arm healthy and increase the life of fistula/stunt. Accordingly, various prior arts have disclosed different type of protective sleeves to protect such sites.

For example, a U.S. Pat. No. 8,419,638 discloses implantable devices for evaluating body-associated fluid transport structures and method of using the same, wherein the implantable devices include an elongated structure with at least one hermetically sealed integrated circuit sensor stably associated therewith and a transmitter.

Another, U.S. Pat. No. 6,276,364 discloses a protective sleeve for a chronically implanted intravenous site {IV) site, wherein the sleeve is made of a prophylactic waterproof material, and is normally worn by a person while showering to prevent moisture from invading the IV site.

Yet another U.S. Pat. No. 5,592,953 discloses protective sleeves for protectively covering an appendage and medical sites such as intravenous equipment, bandages, wounds, etc. The sleeve is open at both ends with adjustable elastic sections, which effectively seal the sleeve against the appendage.

Still another U.S. Pat. No. 6,267,115 discloses a protective device used for an intravenous (IV) site during intravenous infusion includes a waterproof flexible wrap that wraps around a portion of a limb where an intravenous catheter enters a vein.

Another Patent No US20030139792 discloses a fistula thermotherapy device, especially to a fistula thermotherapy device that not only protects the arm with the fistula for hemodialysis, but also facilitates the metabolism of the cells near the needle insertions on fistula. Therefore, to avoid unnecessary suffering of patients due to shunt/fistula placement and reduce the workload of health care personnel, providing a sleeve to protect the arm from external assaults and further providing monitoring of vital signs could help to keep the arm of patient health and avoid any further complication or discomfort to the patient due to fistula/shunt.

Various attempts have been made to solve the problems which may be found in the related art but have thus far been unsuccessful. A need exists for a reliable Vital Sleeve to avoid the above-mentioned problems.

BRIEF SUMMARY OF THE INVENTION

In view of the foregoing disadvantages inherent in the known types of protective sleeves or like in the prior art, the present invention provides an improved vital sleeve that protects the shunt site as well as monitor certain parameters of the body as well. As such, the general purpose of the present invention, which will be described subsequently in greater detail, is to provide a new and improved medical arm sleeve with all the advantages of the prior art and none of the disadvantages.

Accordingly, it is an object of the present invention to provide a medical arm sleeve to protect the fistula/shunt site in arm from external assaults and prevent any kind of infection or other damages caused to the arm.

Another object of the present invention is that the medical arm sleeve that monitors vital signs for keeping the arm healthy and early detection of any abnormal functioning.

A further object of the present invention is that the medical arm sleeve allows remote monitoring of the vital signs.

A still further object of present invention is that the medical arm sleeve is light in weight.

An additional object of present invention is that the medical arm sleeve is comfortable to skin.

Yet another object of present invention is that the medical arm sleeve is easy to wear.

There has thus been outlined, rather broadly, the more important features of the invention in order that the detailed description thereof that follows may be better understood and in order that the present contribution to the art may be better appreciated.

Numerous objects, features, and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. In addition, it is to be understood that the phraseology and terminology employed herein are for the purpose of descriptions and should not be regarded as limiting.

BRIEF DESCRIPTION OF THE DRAWINGS

To further clarify various aspects of some example embodiments of the present invention, a more particular description of the invention will be rendered by reference to specific embodiments thereof, which are illustrated in the appended drawing. It is appreciated that the drawing depicts only illustrated embodiments of the invention and are therefore not to be considered limiting of its scope. The invention will be described and explained with additional specificity and detail through the use of the accompanying drawing in which.

The various embodiments of the present invention will hereinafter be described in conjunction with the appended drawings.

DETAILED DESCRIPTION

The embodiments of the present disclosure described below are not intended to be exhaustive or to limit the disclosure to the precise forms disclosed in the following detailed description. Rather, the embodiments are chosen and described so that others skilled in the art may appreciate and understand the principles and practices of the present disclosure.

The following embodiments and the accompanying drawings, which are incorporated into and form part of this disclosure, illustrate embodiments of the invention, and together with the description, serve to explain the principles of the invention. To the accomplishment of the foregoing and related ends, certain illustrative aspects of the invention are described herein in connection with the following description and the annexed drawings. These aspects are indicative, however, of but a few of the various ways in which the principles of the invention can be employed and the subject invention is intended to include all such aspects and their equivalents. Other advantages and novel features of the invention will become apparent from the following detailed description of the invention when considered in conjunction with the drawings.

In some preferred embodiments, the present invention provides a medical arm sleeve adapted to be worn in arm of a person having implanted fistula/shunt in the arm. The purpose of the invention is to provide a protective, user friendly, easy to wear sleeve for the arm.

Figure 1:
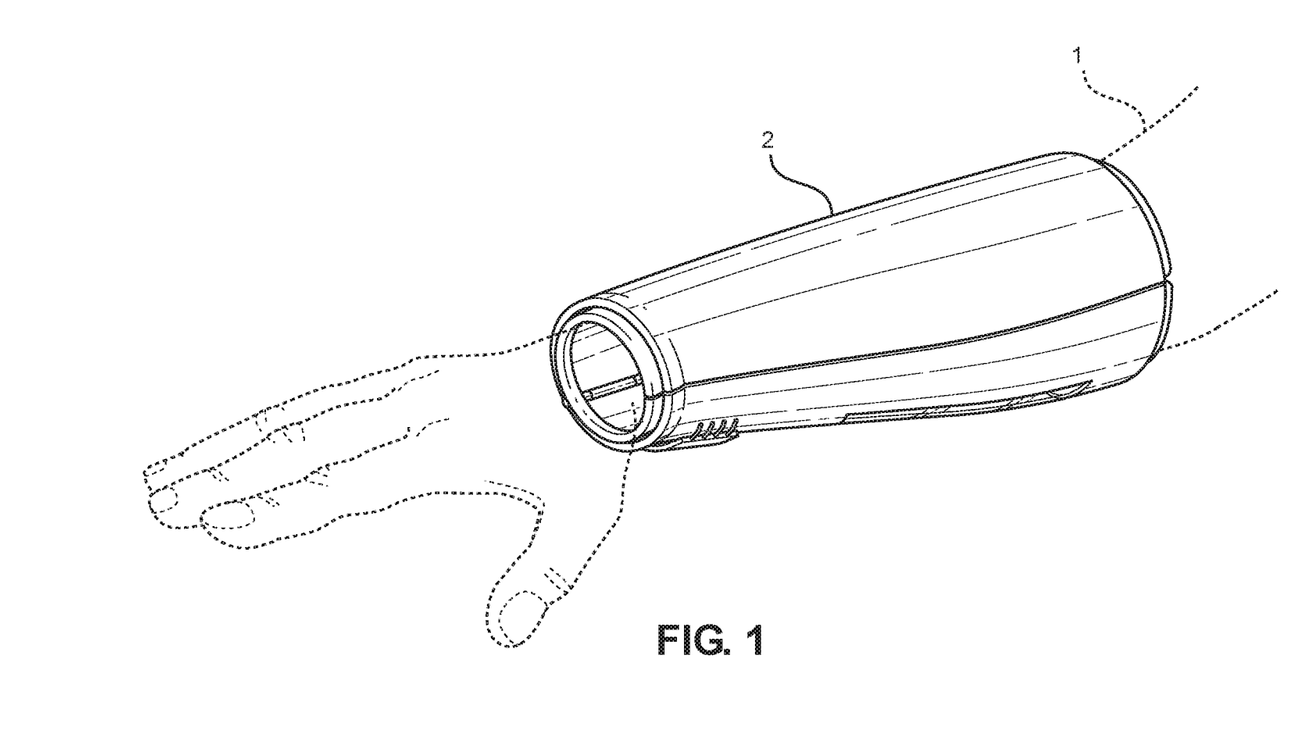
FIG. 1 is a perspective view of the medical arm sleeve worn on an arm.
Figure 2:
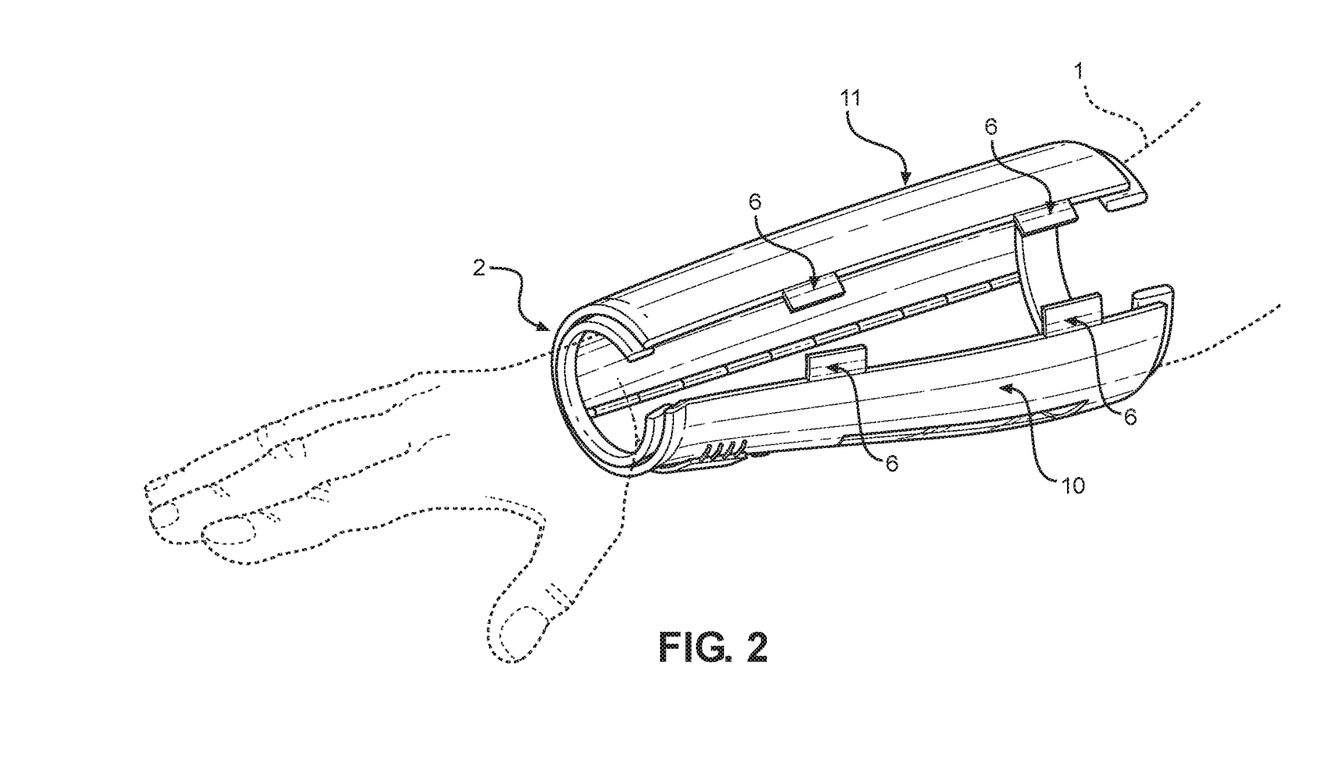
FIG. 2 is a perspective view of the medical arm sleeve in an open position.
Figure 3:
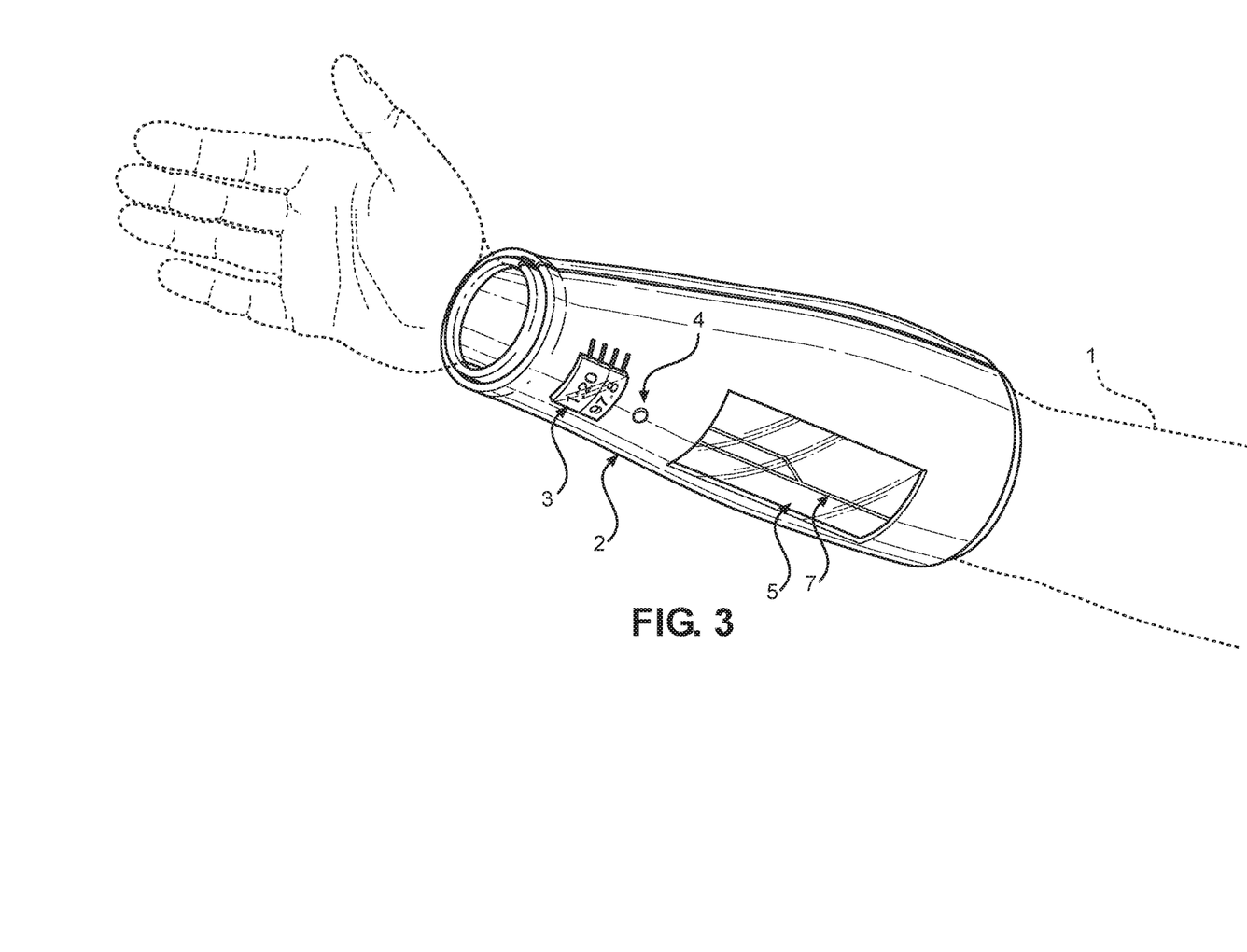
FIG. 3 is a bottom view of the medical arm sleeve showing the display screen and control buttons.
Figure 4:
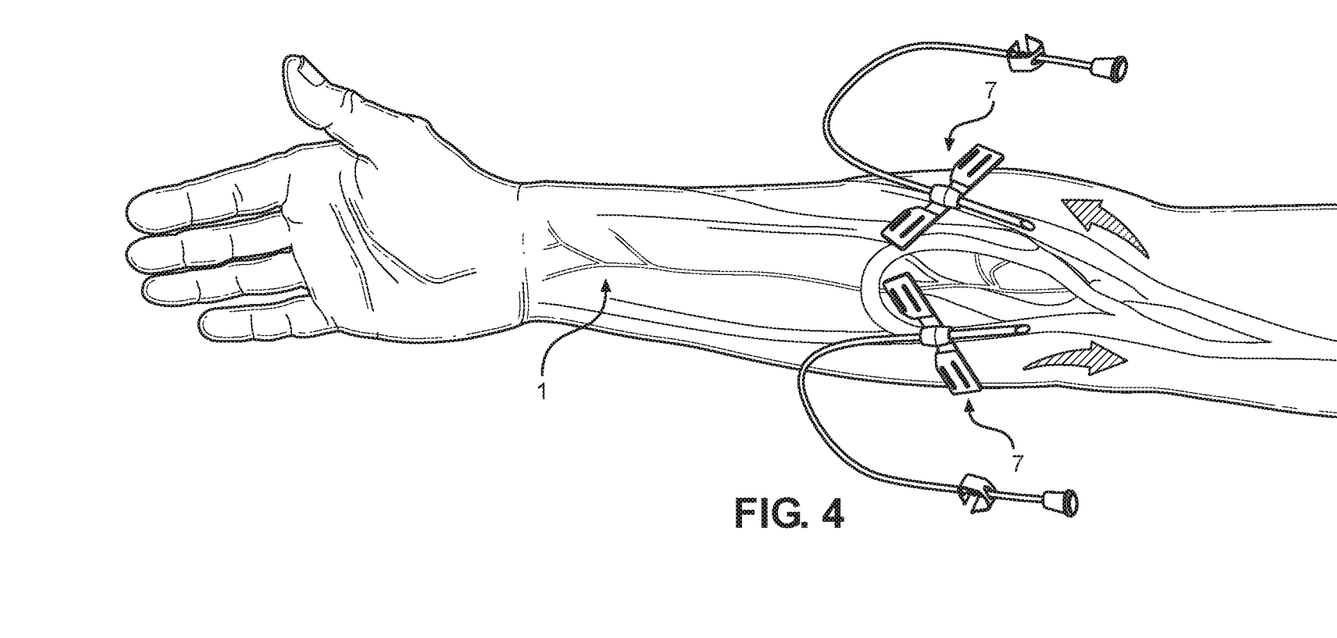
FIG. 4 illustrates two shunts respectively placed within a vein and an artery of a patient before the protective sleeve is applied.
Figure 5:
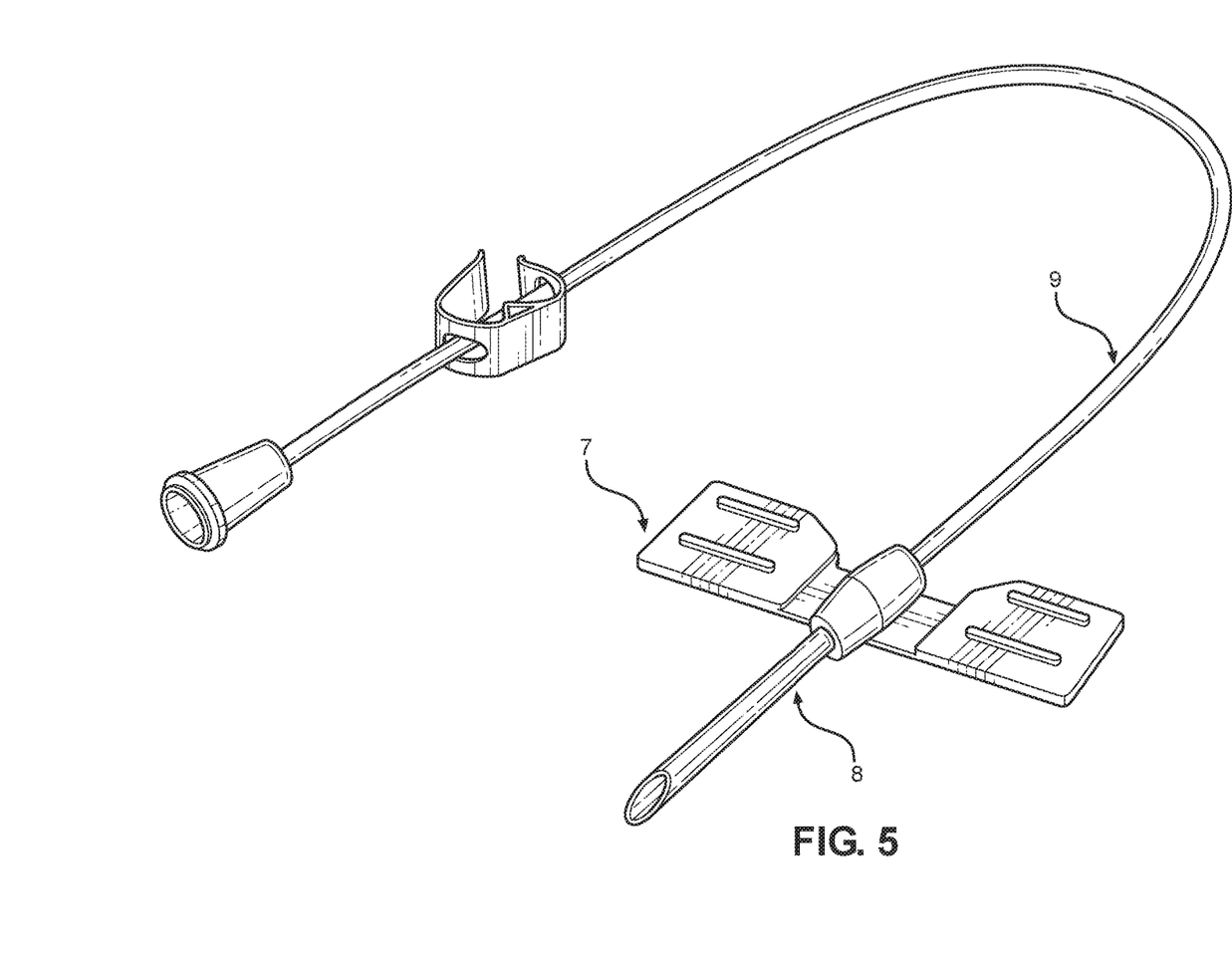
FIG. 5 illustrates a medical shunt including a hollow needle and a vascular tube.
Figure 6:
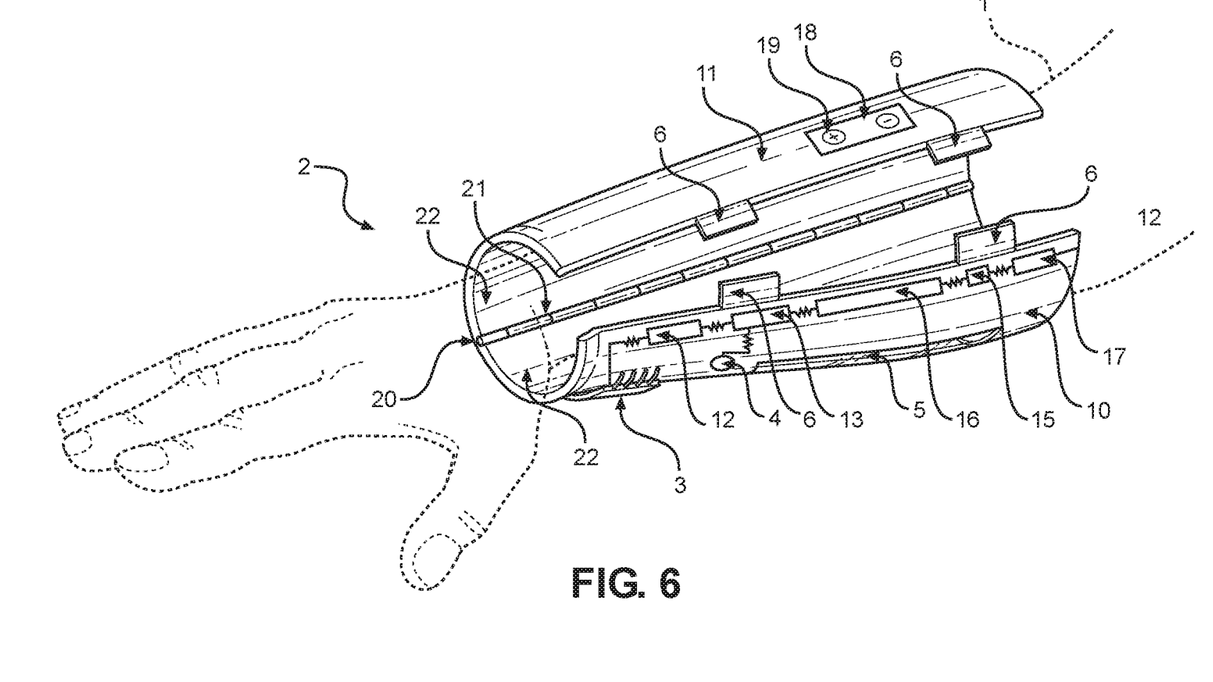
FIG. 6 is a perspective view of the medical arm sleeve of the preferred embodiment.

Turning now descriptively to drawing and referring to FIG. 1-3, which shows a medical arm sleeve worn in the arm 1. The sleeve 2 aims to protect the arm portion having an implanted fistula or shunt 7 against the external assaults. The rectangular shaped sleeve is configured to be worn in a human arm by placing the sleeve over the arm as shown in FIG. 2. The sleeve has fasteners on opposite sides for securing the sleeve over the arm. The fasteners 6 could be hook and loop fastener, snap fit or plug type fasteners wherein one edge of the sleeve includes a male part of the fastener and the opposite edge of sleeve contains a female part of fastener. To secure the sleeve to the arm, the arm is places inside the sleeve with the two open edges of the sleeve facing each other, and one of the edge is pushed towards the other to secure the fastener.

The inner layer of sleeve is made of skin friendly material that is comfortable to skin and may further has moisture wicking properties. Further cushioning is provided in the inner layer for additional comfort and a level of protection against external assaults such as bumps and physical damage on the arm. The outer layer of sleeve is durable to provide additional protection to the arm. Thus, the sleeve fully covers the fistula/shunt site and the person does not have to worry about keeping the arm safe and protected.

In one embodiment, the disclosed medical arm sleeve further include additional feature for monitoring vital signs at the fistula/shunt site. The vital signs include blood pressure, body temperature, pulse rate of the shunt etc. The monitoring of the vital signs helps for early detection of any potential problems to the fistula/shunt. As shown in FIG. 3 the sleeve is provided with a display screen 3 and an inner measuring analytes incorporated within the sleeve, provided the same will monitor pulse or thrill and blood flow rate and display the measured values on the display panel. The display panel could help the patient as well as the doctor to monitor and analyze the parameters and treat the site in case of emergency. An on/off switch 4 is provided to turn the monitoring of vital signs on and off. The button is a simple push type button that could be pressed to start the monitoring and it could be pressed again to turn the monitoring off. The sleeve is further provided with a window 5 positioned over the fistula/shunt site and provide access to the fistula or shunt during dialysis. Preferably, the window has a transparent cover that allows viewing the fistula/shunt site.

In another embodiment, the disclosed sleeve with additional features consisting of connecting the sleeve with a remote computing device to allow the physician to use tele monitoring, and remain updated about the health parameters of the person. The ability of the sleeve to connect to the visual monitor allows for convenient tele monitoring of the shunt site, even if the physician is unable to reach the patient site. The ability to communicate the health parameters to a remote device in real-time allows a concerned medical personal to observer the dialysis remotely, such as from his office and take appropriate action in case any problem occur during dialysis. Thus, the sleeve is capable enough to serve dual functions: protecting the shunt site from any external damage and monitoring of the physiological parameters at the shunt site with convenience to the patient as well as physician.

Additionally, the sleeve is designed to fit in the arm of a person, wherein the physician or supplier could obtain the unique measurements of the person and the exact location of the shunt on the arm. It is advisable to cast the sleeve accordingly, provided the sleeve does not spin about the arm, not constrict the arm at any point, but be able to monitor the vital signs of the patient. Additionally, the provided window should be wide enough for visualizing the shunt site.

In another embodiment, the medical arm sleeve of present invention protects the arm (shunt/fistula} from external assaults to reduce the risk of damage, thereby reducing the need for intervention/hospital readmission/missed dialysis/thrombus (clot}/surgery. This in turn may provide cost savings and increase quality for payers/providers/patients. Therefore, align the invention with the affordable care act/federal and state regulators and HHS, for improving quality outcomes and managing hemodialysis patients.

In a preferred embodiment, best shown in FIGS. 3-6, a combination of the medical shunt 7 and the protective sleeve 2 is set forth wherein the medical shunt 7 comprises at least one hollow needle 8 formed from stainless steel, plastic, or ceramic material, and at least one vascular tube 9 formed from a plastic or rubber material that is removably connected to a respective hollow needle. The medical shunt is adapted to be removably inserted into and out of veins and arteries of a medical patient. The protective sleeve 2 comprises two sleeve portions (10 and 11) movable with respect to one another, such that the protective sleeve can be removably attached to an arm of the medical patient and removably cover and protect the medical shunt and a portion of the medical patient's arm in proximity to the medical shunt; a transparent window 5 connected to one of the two sleeve portions and is adapted to allow a medical practitioner to view the medical shunt and the patient's arm in proximity to the medical shunt through the protective sleeve; an electronic device 13 including a plurality of sensors (12 and 14), a computer member 15, a display panel 3, an alert member 16 adapted to alert the medical practitioner, and a power source 17 electronically connected and provides electric power to the plurality of sensors, the computer member, the display panel, and the alert member; wherein the electronic device is connected to one of the two sleeve portions and is adapted to detect, monitor, and display vital signs of the medical patient; and wherein the electronic device is adapted to detect, monitor, and display measurements of blood flow through the medical shunt; and wherein the electronic device is adapted to emit an alert to the medical practitioner when vital signs and or blood flow fall outside of predetermined values, and wherein any malfunction of the medical shunt or the protective sleeve is detected. The alert member 16 may be formed as a flashing light emitting diode or as an audio speaker. The plurality of sensors (12 and 14) may include a blood flow thrill detector and a blood flow bruit detector. The electronic device 13 may further include a transmitter member adapted to send electronic signals to a remote transceiver to transmit vital signs, measurements of blood flow, and alerts to a remote medical practitioner. The protective sleeve may further comprise a second transparent window 18 connected to one of the two sleeve portions and includes a light emitting diode 19 adapted to flash in unison with the thrill of the blood flow through the medical shunt. The two sleeve portions 10 and 11 of the protective sleeve may include an outer rigid layer thereon adapted to protect the medical shunt from external blunt forces. The outer rigid layers may be formed from plastic or ceramic. The two sleeve portions may be connected via a hinge member 20; and wherein the protective sleeve may further comprise a releasable locking member 6 attached to one of the two sleeve portions that is adapted to releasable lock to the other of the two sleeve portions. The hinge member may be formed as a spring hinge including a spring member 21. The two sleeve portions of the protective sleeve may include a padded inner layer thereon adapted to cushion the medical patient's arm. Furthermore, the two sleeve portions 10 and 11 of the protective sleeve may include an inner layer 22 thereon formed from a textured material adapted to prevent the protective sleeve from moving with respect to the medical patient's arm.

It is to be understood that the medical arm sleeve encompasses various alternative for example the sleeve could be provided in different shapes from square to rectangular. The vital signs monitoring could be varied for example, the sleeve could only provide protection to the arm with no vital sign monitoring; or the sleeve is could include technology that will measure the pulse and blood flow in the fistula. Further the sleeve could have advanced vital sign monitoring obvious to as killed person. The sleeve could be equipped with a GPS device for emergency locating of hemodialysis patients as well. Furthermore, the medical sleeve arm may include various forms of indicia and color.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention.

Although the invention has been explained in relation to its preferred embodiment, it is to be understood that many other possible modifications and variations can be made without departing from the spirit and scope of the invention.

What is claimed is:

1. A combination of a medical shunt and a protective sleeve, comprising:
   a medical shunt comprising:
      at least one hollow needle; and
      at least one vascular tube;
         wherein respective said at least one vascular tube is removably connected to a respective said at least one hollow needle;
      wherein said medical shunt is adapted to be removably inserted into and out of veins and arteries of a medical patient; and
   a protective sleeve comprising:
      two sleeve portions;
         wherein said two sleeve portions are movable with respect to one another, such that said protective sleeve can be removably attached to an arm of said medical patient and removably cover and protect said medical shunt and a portion of said medical patient's arm in proximity to said medical shunt;
      a transparent window;
         wherein said transparent window is connected to one of said two sleeve portions and is adapted to allow a medical practitioner to view said medical shunt and said patient's arm in proximity to said medical shunt through said protective sleeve;
      an electronic device including;
         a plurality of sensors;
         a computer member;
         a display panel;
         an alert member;
            wherein said alert member is adapted to alert said medical practitioner; and
         a power source;

wherein said power source is electronically connected and provides electric power to said plurality of sensors, said computer member, said display panel, and said alert member;

wherein said electronic device is connected to one of said two sleeve portions and is adapted to detect, monitor, and display vital signs of said medical patient; and wherein said electronic device is adapted to detect, monitor, and display measurements of blood flow through said medical shunt; and wherein said electronic device is adapted to emit an alert to said medical practitioner when vital signs and or blood flow fall outside of predetermined values, and wherein any malfunction of said medical shunt or said protective sleeve is detected.

2. The combination of claim 1, wherein said alert member is formed as a flashing light emitting diode.

3. The combination of claim 1, wherein said alert member is formed as an audio speaker.

4. The combination of claim 1, wherein said plurality of sensors includes a blood flow thrill detector.

5. The combination of claim 1, wherein said plurality of sensors includes a blood flow bruit detector.

6. The combination of claim 1, wherein said electronic device further includes a transmitter member adapted to send electronic signals to a remote transceiver to transmit said vital signs, said measurements of blood flow, and said alerts to a remote medical practitioner.

7. The combination of claim 4, wherein said protective sleeve further comprises a second transparent window connected to one of said two sleeve portions and includes a light emitting diode adapted to flash in unison with said thrill of said blood flow through said medical shunt.

8. The combination of claim 4, wherein said two sleeve portions of said protective sleeve include an outer rigid layer thereon adapted to protect said medical shunt from external blunt forces.

9. The combination of claim 8, wherein said two sleeve portions are connected via a hinge member; and wherein said protective sleeve further comprises a releasable locking member attached to one of said two sleeve portions that is adapted to releasable lock to said other of said two sleeve portions.

10. The combination of claim 9, wherein said hinge member is formed as a spring hinge including a spring member.

11. The combination of claim 8, wherein said two sleeve portions of said protective sleeve include a padded inner layer thereon adapted to cushion said medical patient's arm.

12. The combination of claim 8, wherein said two sleeve portions of said protective sleeve include an inner layer thereon formed from a textured material adapted to prevent said protective sleeve from moving with respect to said medical patient's arm.

13. The combination of claim 8, wherein said outer rigid layers of said two sleeve portions of said protective sleeve are formed from a material chosen from a list of materials consisting of plastic and ceramic.

14. The combination of claim 1, wherein said at least one hollow needle of said medical shunt is formed from a material chosen from a list of materials consisting of stainless steel, plastic and ceramic.

15. The combination of claim 1, wherein said at least one vascular tube of said medical shunt is formed from a material chosen from a list of materials consisting of plastic and rubber.

* * * * *